(12) United States Patent
Mahe et al.

(10) Patent No.: US 6,358,929 B1
(45) Date of Patent: Mar. 19, 2002

(54) USE OF A PEPTIDE PREVENTING THE INTOLERANCE REACTIONS OF THE SKIN, IN PARTICULAR IN COSMETIC COMPOSITIONS

(75) Inventors: Yann F. Mahe, Morsang sur Orge; Albert Duranton, Maisons Laffitte, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/410,618

(22) Filed: Oct. 1, 1999

(30) Foreign Application Priority Data

Oct. 1, 1998 (FR) ............................................. 98 12300

(51) Int. Cl.⁷ ............................................... C07K 14/00
(52) U.S. Cl. ............................... 514/18; 574/6; 574/13; 574/14; 574/16; 574/17
(58) Field of Search ............................ 514/13, 14, 18, 514/17, 16, 6

(56) References Cited

U.S. PATENT DOCUMENTS 4,874,744 A  * 10/1989 Nordlund et al. ............. 514/13
5,028,592 A  * 7/1991 Lipton ........................... 514/18
5,739,111 A   4/1998 Mahe ............................ 514/18

FOREIGN PATENT DOCUMENTS

| EP | 0 759 292 A1 | | 2/1997 | | |
| EP | 0 764 444 A1 | | 3/1997 | | |
| EP | 764444 A | * | 3/1998 | .......... | A61K/38/06 |
| WO | WO 88/00833 | | 2/1988 | | |
| WO | 9710838 | * | 3/1997 | .......... | A61K/38/06 |

OTHER PUBLICATIONS

L.A. Rheins, Ph.D. et al., Alpha–Melanocyte Stimulating Hormone Modulates Contact Hypersensitivity Responsiveness in C57/BL6 Mice, The Journal of Investigative Dermatology No. 4, pp. 511–517, (1989).

L.W. Tjoelker et al., Anti–Inflammatory Properties Of A Platelet–Activating Factor Acetylhydrolase, Nature 374, pp. 549–553, (1995).

* cited by examiner

Primary Examiner—Karen Cochrane Carlson
(74) Attorney, Agent, or Firm—Oliff & Berridge, PLC

(57) ABSTRACT

Use as additives, in cosmetic compositions, of a peptide containing the sequence Lysine-Proline-Valine, with the aim of preventing or reducing the intolerance reactions linked to a contact hypersensitivity.

28 Claims, No Drawings

USE OF A PEPTIDE PREVENTING THE INTOLERANCE REACTIONS OF THE SKIN, IN PARTICULAR IN COSMETIC COMPOSITIONS

The invention relates to a method of cosmetic treatment which makes it possible in particular to prevent or reduce the intolerance reactions of the skin, by virtue of the use of a cosmetic composition comprising a particular peptide as additive.

The use of such a peptide as additive in a cosmetic composition makes it possible to reduce the risks of developing contact dermatitis (also called contact eczema) or other skin reactions resulting from a contact hypersensitivity.

It is known that contact hypersensitivity reactions are caused by low-molecular-weight allergens (haptens) which are capable of binding with proteins present in the epidermal cells, including proteins of antigen-presenting cells (Langherans's cells), to form protein-hapten complexes (or conjugates). The antigen-presenting cells of the epidermis then migrate and sensitize T lymphocytes. After a latent period which is about 4 to 5 days, when the site of epidermis again comes into contact with the allergen (triggering reaction), the sensitized T cells migrate to this site and induce the release of cytokines which cause the arrival of macrophages and of nonsensitized T cells which are in turn activated. This influx of cells may result in particular in the formation of an oedema or of vesicles which generally occurs after a few hours or even 1 or 2 days after the triggering reaction in people already sensitized.

Unlike the other allergic reactions, caused by excessive production of immunoglobulins IgE, contact hypersensitivity reactions are mainly linked to a cellular immunological response. Contact hypersensitivity is linked by immunologists to type IV delayed hypersensitivity, also called cell-mediated hypersensitivity.

The sensitizing substances may be very diverse. They are in particular metals or metal salts (chromium, nickel, cobalt, mercury), formalin, synthetic resins (epoxy resins, acrylic and phenolic resins), latexes, medicaments for local application, some cosmetics, dyes or dye precursors (para-phenylenediamine, aniline, aminophencls), pesticides, some synthetic tissues, some plant products (in particular penta-decylcatechols or "poison ivy"), or preservatives.

Thus, many substances are capable of causing contact dermatitis, both in professional life and In daily life.

Contact hypersensitivity. which manifests itself in particular by an irritation, can, in the acute forms, cause an erythema, an oedema, the formation of vesicles, or a pruritus or a burning sensation.

The most serious forms of contact dermatitis require a pharmaceutical treatment with cortico-steroids. The latter are therefore used after a triggering of the hypersensitivity reaction. Their a posteriori therapeutic use, although effective, is therefore curative and not preventive. In addition, their mode of action can cause, in the long term, undesirable effects (in particular lightening of the skin, atrophy of the skin and risk of skin superinfection).

Moreover, it is known that a lot of molecules, of great diversity, are capable of being used as constituents of cosmetic compositions. It is also known that an increase is currently observed in the number of cases of cross-contact hypersensitivity reactions. Thus, the application of cosmetic compositions risks causing such reactions in the users.

It is therefore desirable to be able to have available new agents which make it possible to prevent contact hypersensitivity reactions and to reduce the risks of occurrence of such a reaction in humans, and in particular in people having hypersensitive skins, also called intolerant and/or reactive skins.

The present invention is based on the discovery of the properties of some peptides capable of preventing contact hypersensitivity reactions and of reducing the risks of occurrence of such a reaction. Such an effect is clearly different from an anti-inflammatory effect, as shown, for example, by the experimental section below.

The invention relates more precisely to the use of particular peptides containing the peptide sequence Lysine-Proline-Valine as additives in a cosmetic composition or as active ingredients in the preparation of a medicament intended to suppress or reduce contact hypersensitivity reactions, with the exception of the use of melanotropin. Melanotropin, also called α-MSH, is a known natural peptide having 13 amino acid residues (all of L configuration) and containing, at positions 11 to 13, the peptide sequence indicated.

An activity of modulator of the response to contact hypersensitivity has been described for melano-tropin by RUEINS et al., J. Invest. Dermatol. 93, 511–517 (1989).

Each of the amino acid residues of the peptides used according to the present invention may be of any configuration, L or D.

The subject of the invention is therefore a method of cosmetic treatment, characterized in that, with the aim of preventing or reducing the intolerance reactions of the skin linked to a contact hypersensitivity, a customary cosmetic composition containing, as additive, at least one peptide containing the peptide sequence Lysine-Proline-Valine, with the exception of melano-tropin, or a derivative of such a peptide, is applied to the skin or the superficial body growths.

"Superficial body growths" are understood to mean the hair, the nails and the body hair (in particular eyelashes and eyebrows).

The method of cosmetic treatment of the invention is intended for particular for people having hypersensitive or intolerant skin.

The subject of the invention is also the use, as active ingredient, in the preparation of a medicament intended for combating (preventatively or curatively) contact hypersensitivity reactions, of at least one peptide (or of a derivative of such a peptide) containing the peptide sequence Lysine-Proline-Valine, as defined above, with the exception of the use of melanotropin.

The peptide used according to the invention may contain in particular from 3 to 10 amino acid residues, and in particular 3, 4, 5 or 6 amino acid residues, which may each be, independently, of L or D configuration.

By way of example, at least one amino acid residue of the peptide, in particular at least one amino acid residue of the peptide sequence Lysine-Proline-Valine, and in particular the proline residue, may have the D configuration. The invention includes the use of peptides as defined above, in which the amino acid residues constituting the peptide sequence Lysine-Proline-Valine all have the D configuration. The peptides used according to the invention are in particular those in which, in addition, at least part (including all) of the amino acid residues other than those of the sequence Lys-Pro-Val have the D configuration.

The invention relates in particular to the use of peptides containing at least the peptide sequence of formula I:

Lys-Pro-Val          (I)

as well as the use of derivatives of these peptides, with the exception of the use of melanotropin. The derivatives of the peptides containing the sequence of formula I are for example those in which at least one functional group (in particular the amine and carboxyl groups), is protected with a protecting group. Of course, the protecting group should be compatible with a use in the cosmetics or pharmaceutical field. The customary protecting groups are well known. The peptide derivatives comprise in particular those for which the terminal carboxyl group and the other carboxyl groups which may be present are in the form of an ester (for example lower alkyl ester) or of an amide, and/or those for which the N-terminal amine group and the other amine groups which may be present are in acylated (for example acetylated) form. More generally, the derivatives of the peptides containing the peptide sequence of formula I include not only the addition salts with carboxylic organic acids, and not only the acetates, but also other addition salts such as for example the trifluoroacetates, as well as the addition salts with inorganic acids such as the sulphates, hydrochlorides and the like. The derivatives also include the salts resulting from the salivation of the carboxyl group (or of the carboxyl groups), and in particular the salts of alkali metals or alkaline earth metals such as the salts of sodium or of calcium.

Among the peptides which can be used according to the invention, there may be mentioned in particular those in which the Val residue, in the Lys-Pro-Val sequence, constitutes the C-terminal end of this sequence, and in particular those for which the Lys-Pro-Val sequence constitutes the C-terminal end of the peptide (the C-terminal amino acid being Val). There may be mentioned, by way of examples, the peptides which contain at least one of the following tripeptide sequences: D-Lys-D-Pro-D-Val, D-Lys-D-Pro-L-Val, L-Lys-D-Pro-D-Val or L-Lyt-D-Pro-L-Val. The tripeptides formed by the sequences which have just been mentioned are called peptides of formula Ia, Ib, Ic and Id, respectively.

The derivative of the peptide of formula Ia whose lysine residue is acetylated and whose carboxyl group of the valine residue is amidated is symbolized by the formula II:

Ac-D-Lys-D-Pro-D-Val-NH$_2$    (II)

The peptides used according to the invention, and their derivatives, may be prepared according to the customary peptide synthesis techniques.

The compositions containing the peptide used according to the invention may be administered by the oral, parenteral or topical route.

To this effect, they may be presented in particular in the form of tablets, gelatin capsules, oral solutions, injectable solutions, lyophilizates for injectable solutions, lotions, gels or liquid or semi-solid emulsions.

Such compositions contain the peptide used according to the invention at concentrations which may generally vary from $10^{-12}$ M to $10^{-2}$ M, and in particular from $10^{-7}$ M to $10^3$ M.

These compositions are prepared according to the customary methods.

The pharmaceutical compositions obtained according to the invention contain, in addition to the active ingredient, optionally combined with other active ingredients, at least one appropriate pharmaceutical vehicle.

The invention also relates to the use of at least one peptide or peptide derivative, as defined above, in cosmetic compositions (in particular compositions for the skin, for the nails or for the hair), as additive intended to eliminate or reduce the risks of contact hypersensitivity reactions for the users of the composition. This involves reducing both he risks of a reaction to potentially sensitizing external agents and the risks of a reaction to the substances present in the cosmetic composition which constitute potential allergens.

The cosmetic compositions thus obtained contain, in addition to the peptide, the customary ingredients and vehicles present in the type of composition envisaged. These compositions are in particular lotions, creams or gels for the face, the neck or the hands, lipsticks, make-up, make-up-removing or skin cleansing compositions, mascaras, foundations, powders for the face, soaps, perfumes, nail varnishes or hair compositions such as shampoos, hair lotions, hair-dyeing compositions, permanent waving compositions for the hair, and the like.

The advantage of the presence of a peptide used according to the invention in compositions for the hair obviously results from the fact that during use, these compositions are most often in contact with the scalp, hence a risk of contact allergy. In the case of compositions for nails, the advantage is that often the nails are in contact with the skin.

In the experimental part below, the acronym TNCB designates trinitrochlorobenzene.

PHARMACOLOGICAL STUDY

1) Study of the Effect of the Peptide of Formula II on the Response to Sensitization by TNCB, on the Mouse a) Reduction in the contact hypersensitivity reaction after sensitization The study is carried out on 7-to 10-week-old female Balb/C mice.

A dose of 1.5 μg of the peptide studied (in solution in PBS buffer containing 0.1% of mouse serum) is injected into a vein of the tail of the mice 2 hours before the sensitization reaction.

The sensitization reaction consists in applying, with a brush, 100 μl of a solution containing 0.15% of TNCB in an acetone-olive oil (4:1) mixture to the shaved skin of the abdomen of the mice.

The triggering reaction is carried out 7 days after the sensitization reaction. This triggering reaction consists in applying to the two sides of an ear 10 microlitres of a solution containing 0.8% of TNCB in a vehicle consisting of the acetone-olive oil mixture already mentioned above.

To the other ear, only this mixture of acetone and olive oil is applied, for comparison.

The intensity of a possible contact hypersensitivity reaction is evaluated by estimating the size of the oedema of the ear treated with TNCB, in comparison with the ear treated with the vehicle alone. For that, the thickness of the ears is measured and compared with the aid of a micrometer screw. This measurement is carried out 24 hours after the triggering reaction.

The TNCB is also applied to the ear of control mice which have not been previously sensitized (negative controls).

The positive controls do not receive the peptide before the sensitization reaction.

Results

In this experiment, the increase in the thickness of the ear in the positive controls is on average $9.8 \times 10^{-2}$ mm. In the negative controls, this increase is of the order of $1 \times 10^{-2}$ mm. For the animals treated with the peptide studied, this increase is only about $2.5 \times 10^{-2}$ mm.

These results show that the peptide studied greatly reduces the contact hypersensitivity reaction.

b) Reduction of the contact hypersensitivity reaction after a second sensitization 14 days after the end of the experiment described in a) above, the same mice are subjected to a new sensitization reaction on the shaved skin of the back, as described in a).

7 days later, the triggering test is carried out by application of TNCB to the ear, and 24 hours later, the degree of swelling of the ear is measured.

The aim of this second experiment is to distinguish between a possible a specific temporary immunosuppression and a specific immunological tolerance.

Results

For the positive controls, the average increase in the thickness of the ear is of the order of $14 \times 10^{-2}$ mm. For the animals which had been treated with the peptide II in the first experiment, just as for the negative controls, the degree of swelling of the ear is of the order of $3.5 \times 10^{-2}$ mm.

These results show that the animals treated with the peptide studied before the first sensitization did not develop a contact hypersensitivity after application of a second sensitizing dose of TNCB. The mice thus treated therefore became tolerant to TNCB.

c) Effect off the peptide of formula II in topical application

The procedure is carried out as in a) above, but the peptide, incorporated in a cream of the water-in-oil type, is applied to the area to be sensitized 2 hours before the sensitization.

24 hours after the triggering reaction, the increase in the thickness of the ear is on average $3 \times 10^{-2}$ mm in the treated mice and $7 \times 10^{-2}$ mm in the positive controls.

2) Study of the Effect by the Topical Route in Humans

This study was carried out on 18 to 65 year-old volunteer patients in whom a contact allergy to nickel was suspected. These patients were free from other skin diseases, and the results of this study show that they were not allergic to the constituents of the cream used as vehicle.

On day 0, there are applied with an occlusive dressing, to areas of the skin of the back, on the one hand a cream containing 100 $\mu$M of the peptide of formula II, and on the other hand the cream alone, without peptide, used as placebo.

Two hours later, patches impregnated with petroleum jelly containing nickel sulphate at a concentration of 5% are applied to the same areas of the skin, and also to an adjacent area that has not been pretreated.

24 hours later, the patients are examined. Those who developed a contact hypersensitivity reaction over the area treated with the placebo (and also over the adjacent area which received only the application of nickel salt), and who are therefore people who were already sensitized to nickel, are 14 in number. Out of these 14 people, 7 did not develop any contact hypersensitivity reaction over the area treated with the peptide.

These results show that the peptide studied acts locally, on the site of application, since the adjacent skin area which received only the application of nickel salt indeed gave rise to a contact hypersensitivity reaction.

EXAMPLE OF COMPOSITIONS

Example 1

Lotion for the Scalp

Peptide of formula II . . . $12.5 \times 10^{-6}$ g 2,4-Diarminopyrmidine 3-oxide . . . 0.75 g Ethanol at 95% . . . 30 g Perfume . . . qs Colorants . . . qs Demineralized water . . . qs 100 g Example 2

Care Cream for the Skin (oil-in-water emulsion)

Mixture (80:20) of cetylstearyl alcohol and oxyethylenated cetylstearyl alcohol containing 33 moles of oxyethylene . . . 5 g Glycerol monostearate . . . 1.5 g Cetyl alcohol . . . 0.75 g Liquid paraffin . . . 10 g Polydimethylsiloxane . . . 0.75 g Glycerin . . . 4 g Preservatives . . . qs Peptide of formula II . . . 5 mg Demineraiized water . . . qs 100 g Example 3

Solution Injectable by the Intradermal Route

Peptide of formula II . . . 0.7 mg

Apyrogenic sterile aqueous solution containing 9% of NaCl . . . qs 1 ml

What is claimed is:

1. Method of cosmetic treatment, comprising preventing or reducing intolerance reactions linked to a contact hypersensitivity, by applying to skin or a superficial body growth of an individual suspected of having or being prone to a contact hypersensitivity a cosmetic composition containing, as additive, at least one non-melanotropin peptide or peptide derivative containing the peptide sequence Lysine-Proline-Valine.

2. Method according to claim 1, in which the peptide or peptide derivative contains from 3 to 10 amino acid residues.

3. Method according to claim 1, in which the peptide or peptide derivative contains from 3 to 6 amino acids residues.

4. Method according to claim 1, in which at least one amino acid residue of said peptide sequence has the D configuration.

5. Method according to claim 4, wherein said peptide residue is a proline residue.

6. Method according to claim 1, in which all the amino acid residues of said peptide sequence Lysine-Proline-Valine have the D configuration.

7. Method according to claim 1, in which all amino acid residues of the peptide or peptide derivative have the D configuration.

8. Method according to claim 1, in which said peptide derivative is a peptide in which at least one functional group is protected with a protecting group.

9. Method according to claim 8, wherein at least one carboxyl group of the peptide is protected with a protecting group.

10. Method according to claim 9, wherein a terminal carboxyl group of the peptide is protected with a protecting group.

11. Method according to claim 9, wherein the protecting group forms an ester or an amide.

12. Method according to claim 8, wherein at least one amine group of the peptide is protected with a protecting group.

13. Method according to claim 12, wherein a terminal amine group of the peptide is protected with a protecting group.

14. Method according to claim 12, wherein said amine group is acylated.

15. Method according to claim 14, wherein said amine group is acetylated.

16. Method according to claim 1, in which said additive is the tripeptide D-Lys-D-Pro-D-Val or a derivative thereof.

17. Method according to claim 1, in which said skin or superficial body growth is skin or a superficial body growth of a person having hypersensitive skin.

18. Method according to claim 1, in which said cosmetic composition is applied in the form of a lotion, cream or gel to a face, neck or hands.

19. Method according to claim 1, in which said cosmetic composition is applied to hair in the form of a shampoo, hair lotion, hair dyeing composition or permanent waving composition.

20. Method according to claim 1, in which said cosmetic composition is applied to nails in the form of a nail vanish.

21. Method according to claim 1, in which said peptide derivative is a salt of a peptide.

22. Method according to claim 21, wherein the salt is formed by reaction with a carboxylic organic acid.

23. Method according to claim 21, wherein the salt is formed by reaction with an inorganic acid.

24. Method according to claim 21, wherein said salt results from the salification of at least one carboxyl group of the peptide.

25. Method according to claim 21, wherein said peptide derivative is an alkali metal or alkaline earth metal salt.

26. Method for combating a hypersensitivity reaction, comprising administering or applying to a patient experiencing a contact hypersensitivity reaction a composition containing at least one non-melanotropin peptide or peptide derivative containing the peptide sequence Lysine-Proline-Valine to prevent or reduce said contact hypersensitivity reaction.

27. Method according to claim 26, wherein said composition is applied to an area of skin of said patient reacting to a contact hypersensitivity.

28. Method of preventing or reducing intolerance reactions linked to a contact hypersensitivity, comprising applying to skin or a superficial body growth of an individual suspected of having, or being prone to a contact hypersensitivity or to an individual experiencing a contact hypersensitivity reaction a composition containing at least one non-melanotropin peptide or peptide derivative containing the peptide sequence Lysine-Proline-Valine.

* * * * *

(12) EX PARTE REEXAMINATION CERTIFICATE (4987th)
United States Patent
Mahe et al.

(10) Number: US 6,358,929 C1
(45) Certificate Issued: Sep. 7, 2004

(54) USE OF A PEPTIDE PREVENTING THE INTOLERANCE REACTIONS OF THE SKIN, IN PARTICULAR IN COSMETIC COMPOSITIONS

(75) Inventors: Yann F. Mahe, Morsang sur Orge (FR); Albert Duranton, Maisons Laffitte (FR)

(73) Assignee: L'Oreal, Paris (FR)

Reexamination Request:
No. 90/006,509, Jan. 6, 2003

Reexamination Certificate for:
Patent No.: 6,358,929
Issued: Mar. 19, 2002
Appl. No.: 09/410,618
Filed: Oct. 1, 1999

(30) Foreign Application Priority Data

Oct. 1, 1998 (FR) .............................. 98 12300

(51) Int. Cl.[7] .............................................. C07K 14/00
(52) U.S. Cl. .............................. 514/18; 514/6; 514/13; 514/14; 514/16; 514/17
(58) Field of Search ............... 514/6, 13, 14, 514/16, 17, 18

(56) References Cited

U.S. PATENT DOCUMENTS

| 4,874,744 | * | 10/1989 | Nordlund et al. | .............. 514/13 |
| 5,028,592 | * | 7/1991 | Lipton | .......................... 514/18 |
| 5,157,023 | | 10/1992 | Lipton | |
| 5,739,111 | | 4/1998 | Mahe | .......................... 514/18 |

FOREIGN PATENT DOCUMENTS

| EP | 0 759 292 A1 | 2/1997 | | |
| EP | 0 764 444 A1 | 3/1997 | | |
| EP | 764444 A | * 3/1998 | .......... | A61K/38/06 |
| WO | WO 88/00833 | 2/1988 | | |
| WO | PCT/FR96/01283 | 3/1997 | | |
| WO | 9710838 | * 3/1997 | .......... | A61K/38/06 |

OTHER PUBLICATIONS

Groot and Frosch, Adverse Reactions to Fragrances (1997) Contact Dermatitis, vol. 36, pp. 57–86.*
Sainio et al. (1997) Contact Dermatitis, vol. 37, No. 4, pp. 155–162.*
Sigma Chemical Company, Catalog of Biochemicals, Organic Compounds, and Diagnostic Reagents (1996) p. 1112.*
Thomas E. Creighton, *Proteins—Structures and Molecular Properties,* p. 156 (1993).
Thomas B. Fitzpatrick et al., *Color Atlas and Synopsis of Clinical Dermatology,* pp. 6–9, 11, 13–27, 29–35, 37 (1983).
M.E. Hiltz et al., Anti–Inflammatory Activity of α–MSH (11–13) Analogs; Influences of Alteration in Stereochemistry, *Peptides,* vol. 12, pp. 767–771 (1991).
Melanie E. Hiltz et al., Alpha–MSH Peptides Inhibit Acute Inflammation and Contact Sensitivity, *Peptides,* vol. 11, pp. 979–982 (1990).
James M. Lipton, Ph.D., Modulation of Host Defense by the Neuropeptide α–MSH, *The Yale Journal of Biology and Medicine,* vol. 63, pp. 173–182 (1990).
Ruth L. Memmler et al., *The Human Body in Health & Disease,* pp. 73–81 (1996).
*The American Heritage College Dictionary,* Third Ed. pp. 277, 1002 (Houghtn Mifflin Company, 1997.).
L.A. Rheins, Ph.D. et al., *Alpha–Melanocyte Stimulating Hormone Modulates Contact Hypersensitivity Responsiveness in C57/BL6 Mice,* The Journal of Investigative Dermatology No. 4, pp. 511–517, (1989).
L.W. Tjoelker et al., *Anti–Inflammatory Properties of a Platelet–Activating Factor Acetylhydrolase,* Nature 374, pp. 549–553, (1995).

* cited by examiner

*Primary Examiner*—Karen Cochrane Carlson

(57) ABSTRACT

Use as additives, in cosmetic compositions, of a peptide containing the sequence Lysine-Proline-Valine, with the aim of preventing or reducing the intolerance reactions linked to a contact hypersensitivity.

US 6,358,929 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 26 and 27 are cancelled.

Claims 1, 5 and 28 are determined to be patentable as amended.

Claims 2–4 and 6–25, dependent on an amended claim, are determined to be patentable.

New claims 29–50 are added and determined to be patentable.

1. Method of cosmetic treatment, comprising preventing or reducing *risks of occurrence of* intolerance reactions linked to a contact hypersensitivity, by applying to skin or a superficial body growth of an individual [suspected of having or being] prone to *or suspected of being prone to* a contact hypersensitivity, *but not experiencing a contact hypersensitivity reaction,* a cosmetic composition containing, as additive, at least one non-melanotropin peptide or peptide derivative containing the peptide sequence Lysine-Proline-Valine.

5. Method according to claim 4, wherein said [peptide] *amino acid* residue is a proline residue.

28. Method of preventing or reducing *risks of occurrence of* intolerance reactions linked to a contact hypersensitivity, comprising applying to skin or a superficial body growth of an individual [suspected of having, or being] prone to *or suspected of being prone to* a contact hypersensitivity [or to an individual experiencing a contact hypersensitivity reaction], *but not experiencing a contact hypersensitivity reaction,* a composition containing at least one non-melanotropin peptide or peptide derivative containing the peptide sequence Lysine-Proline-Valine.

*29. Method according to claim 28, in which the peptide or peptide derivative contains from 3 to 10 amino acid residues.*

*30. Method according to claim 28, in which the peptide or peptide derivative contains from 3 to 6 amino acid residues.*

*31. Method according to claim 28, in which at least one amino acid residue of said peptide sequence has the D configuration.*

*32. Method according to claim 31, wherein said amino residue is a proline residue.*

*33. Method according to claim 28, in which all the amino acid residues of said peptide sequence Lysine-Proline-Valine have the D configuration.*

*34. Method according to claim 28, in which all amino acid residues of the peptide or peptide derivative have the D configuration.*

*35. Method according to claim 28, in which said peptide derivative is a peptide in which at least one functional group in protected with a protection group.*

*36. Method according to claim 35, wherein at least one carboxyl group of the peptide is protected with a protecting group.*

*37. Method according to claim 36, wherein a terminal carboxyl group of the peptide is protected with a protecting group.*

*38. Method according to claim 37, wherein the protecting group forms an ester or an amide.*

*39. Method according to claim 35, wherein at least one amine group of the peptide is protected with a protecting group.*

*40. Method according to claim 39, wherein a terminal amine group of the peptide is protected with a protecting group.*

*41. Method according to claim 39, wherein said amine group is acylated.*

*42. Method according to claim 41, wherein said amine group is acetylated.*

*43. Method according to claim 28, in which said peptide or peptide derivative is the tripeptide D-Lys-D-Pro-D-Val or a derivative thereof.*

*44. Method according to claim 28, in which said skin or superficial body growth is skin or a superficial body growth of a person having hypersensitive skin.*

*45. Method according to claim 28, in which said peptide derivative is a salt of a peptide.*

*46. Method according to claim 45, wherein the salt is formed by reaction with a carboxylic organic acid.*

*47. Method according to claim 45, wherein the salt is formed by reaction with an inorganic acid.*

*48. Method according to claim 45, wherein said salt results from the salification of at least one carboxyl group of the peptide.*

*49. Method according to claim 45, wherein said peptide derivative is an alkali metal or alkaline earth metal salt.*

*50. Method according to claim 28, wherein said composition is a pharmaceutical composition.*

\* \* \* \* \*